(12) United States Patent
Charrier et al.

(10) Patent No.: US 7,968,716 B2
(45) Date of Patent: Jun. 28, 2011

(54) CASPASE INHIBITORS AND USES THEREOF

(75) Inventors: Jean-Damien Charrier, Wantage (GB); Guy Brenchley, Wantage (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/883,424

(22) Filed: Sep. 16, 2010

(65) Prior Publication Data
US 2011/0003824 A1 Jan. 6, 2011

Related U.S. Application Data

(62) Division of application No. 12/165,952, filed on Jul. 1, 2008, now Pat. No. 7,829,561, which is a division of application No. 09/877,832, filed on Jun. 7, 2001, now Pat. No. 7,407,964.

(60) Provisional application No. 60/209,929, filed on Jun. 7, 2000.

(51) Int. Cl.
| | |
|---|---|
| *C07D 487/04* | (2006.01) |
| *C07D 487/14* | (2006.01) |
| *A61K 31/5025* | (2006.01) |
| *A61K 31/4985* | (2006.01) |
| *A61P 19/02* | (2006.01) |
| *A61P 39/00* | (2006.01) |

(52) U.S. Cl. ........... 546/79; 546/101; 514/290; 514/294
(58) Field of Classification Search ............ 546/79, 546/101; 514/290, 294
See application file for complete search history.

(56) References Cited

U.S. PATENT DOCUMENTS 7,407,964 B2 * 8/2008 Charrier et al. .......... 514/267
7,829,561 B2 * 11/2010 Charrier et al. .......... 514/248

FOREIGN PATENT DOCUMENTS

| WO | 9533751 | 12/1995 |
| WO | 9535308 | 12/1995 |
| WO | 9811109 | 3/1998 |

OTHER PUBLICATIONS

Wolft, Manfred E., "Burger's Medicinal Chemistry, 5ed, Part 1", John Wiley & Sons, 975-977, (1995).
Banker, G.S. et al., "Modern Pharmaceutics, 3ed", Marcel Dekker, New York, 451-596, (1996).
Reed et al., "Current Opinion in Biotechnology", 11:586-592, (2000).
Nicholson, D.W., Nature, 607, 810-816, (2000).
Cecil Textbook of Medicine, edited by Bennet, J.C. and Plum F., 20th edition, vol. 1, 1004-1010, (1996).
Freshney et al., Culture of Animal Cells, A Manual of Basic Technique, Alan R. Liss, Inc., 1983, New York, p4.
Dermer et al., Bio/Technology, 12:320, (1994).
Golub et al., Science, 286, 531-537, (1999).

* cited by examiner

*Primary Examiner* — Venkataraman Balasubramanian
(74) *Attorney, Agent, or Firm* — Jennifer G. Che

(57) ABSTRACT

This invention provides novel caspase inhibitors of formula I:

wherein $R^1$ is hydrogen, $CHN_2$, R, or —$CH_2Y$; R is an aliphatic group, an aryl group, an aralkyl group, a heterocyclyl group, or a heterocyclylalkyl group; Y is an electronegative leaving group; $R^2$ is $CO_2H$, $CH_2CO_2H$, or esters, amides or isosteres thereof; $X_2$—$X_1$ is $N(R^3)$—$C(R^3)$, $C(R^3)_2$—$C(R^3)$, $C(R^3)_2$—N, N=C, $C(R^3)$=C, C(=O)—N, or C(=O)—C ($R^3$); each $R^3$ is independently selected from hydrogen or $C_{1-6}$ aliphatic; Ring C is a fused aryl ring; n is 0, 1 or 2; and each methylene carbon in Ring A is optionally and independently substituted by =O, or one or more halogen, $C_{1-4}$ alkyl, or $C_{1-4}$ alkoxy. The compounds are useful for treating caspase-mediated diseases.

9 Claims, No Drawings

CASPASE INHIBITORS AND USES THEREOF

CROSS-REFERENCE TO RELATED APPLICATIONS

This application is a divisional of U.S. patent application Ser. No. 12/165,952, filed Jul. 1, 2008, now U.S. Pat. No. 7,829,561, which is a divisional of U.S. patent application Ser. No. 09/877,832, filed Jun. 7, 2001, now U.S. Pat. No. 7,407,964, which claims priority to U.S. Provisional Patent Application 60/209,929 filed Jun. 7, 2000, the contents of which are incorporated herein by reference.

FIELD OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science,* 1998, 281, 1283-1312; Ellis et al., *Ann. Rev. Cell. Biol.,* 1991, 7, 663).

Caspases are a family of cysteine protease enzymes that are key mediators in the signaling pathways for apoptosis and cell disassembly (Thornberry, *Chem. Biol.,* 1998, 5, R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

A four amino acid sequence primarily recognized by the caspases has been determined for enzyme substrates. Talanian et al., *J. Biol. Chem.* 272, 9677-9682, (1997); Thornberry et al., *J. Biol. Chem.* 272, 17907-17911, (1997). Knowledge of the four amino acid sequence primarily recognized by the caspases has been used to design caspase inhibitors. Reversible tetrapeptide inhibitors have been prepared having the structure $CH_3CO-[P4]-[P3]-[P2]-CH(R)CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149-155 (1997); Mjalli, et al., *Bioorg. Med. Chem. Lett.* 3, 2689-2692 (1993); Nicholson et al., *Nature* 376, 37-43 (1995). Irreversible inhibitors based on the analogous tetrapeptide recognition sequence have been prepared where R is an acyloxymethylketone $-COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J Med. Chem.* 37, 563-564 (1994).

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock. Yaoita et al., *Circulation,* 97, 276 (1998); Endres et al., *J Cerebral Blood Flow and Metabolism,* 18, 238, (1998); Cheng et al., J. Clin. Invest., 101, 1992 (1998); Yakovlev et al., *J Neuroscience,* 17, 7415 (1997); Rodriquez et al., *J. Exp. Med.,* 184, 2067 (1996); Grobmyer et al., *Mol. Med.,* 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

Recognizing the need to improve the pharmacological properties of the peptidic caspase inhibitors, peptidomimetic and non-natural amino acid peptide inhibitors have been reported.

EP618223 discloses peptides inhibiting interleukin 1-beta release of the formula:

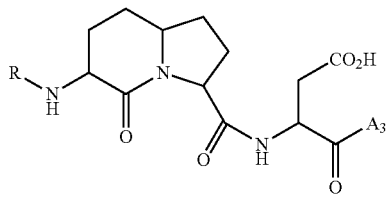

wherein R is a hydrogen, an amino or hydroxy protecting group or optionally ring substituted benzyloxy, $A_3$ is —$CH_2$—$X_1$—CO—$Y_1$; —$CH_2$—O—$Y_2$; or —$CH_2$—S—$Y_3$; wherein $X_1$ is O or S and $Y_1$, $Y_2$, and $Y_3$ are as defined in the specification.

WO 97/22619 discloses ICE inhibitors which contain a piperazic acid unit:

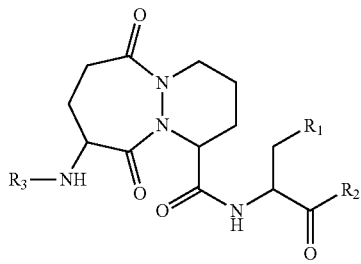

wherein $R_1$ is $CO_2H$ or a bioisosteric replacement of $CO_2H$; $R_2$ is H, alkyl, aryl, heteroaryl, or $CH_2Y$; $R_3$ is H, R, COOR, $CON(R)_2$, $SO_2R$, $SO_2NHR$, $COCH_2OR$, COCOR, COCOOR or $COCON(R)_2$; Y is OR, SR, or —OC=O(R); and R is H, aromatic or alkyl group.

WO 9816502 discloses ICE inhibitors which contain a proline unit:

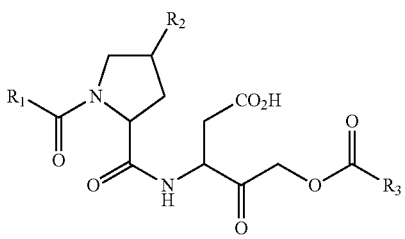

wherein $R_1$ is alkyl or $N(R_3)_2$; $R_2$ is H, or $OCH_2Aryl$; and $R_3$ is selected from various groups.

Dolle et al. (*J. Med. Chem.* 37, 563, (1994)) report ICE inhibitors which contain a pipecolic acid unit:

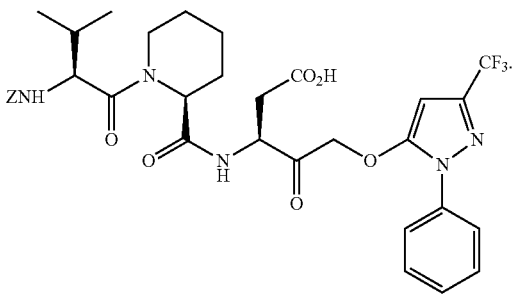

While a number of caspase inhibitors have been reported, it is not clear whether they possess the appropriate pharmacological properties to be therapeutically useful. Therefore, there is a continued need for small molecule caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are effective as inhibitors of caspases and cellular apoptosis. These compounds have the general formula I:

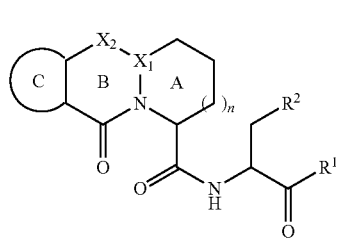

wherein:
$R^1$ is hydrogen, $CHN_2$, R, or —$CH_2Y$;
R is an aliphatic group, an aryl group, an aralkyl group, a carbocyclyl group, a carbocyclylalkyl group, a heterocyclyl group, or a heterocyclylalkyl group;
Y is an electronegative leaving group;
$R^2$ is $CO_2H$, $CH_2CO_2H$, or esters, amides or isosteres thereof;
$X_2$—$X_1$ is $N(R^3)$—$C(R^3)$, $C(R^3)_2$—$C(R^3)$, $C(R^3)_2$—N, N=C, $C(R^3)$=C, C(=O)—N, or C(=O)—$C(R^3)$;
each $R^3$ is independently selected from hydrogen or $C_{1-6}$ alkyl,
Ring C is a fused aryl ring;
n is 0, 1 or 2; and
any methylene position in Ring A is optionally and independently substituted by =O, or one or two groups selected from halogen, $C_{1-4}$ alkyl, or $C_{1-4}$ alkoxy.

The compounds of this invention have potent inhibition properties across a range of caspase targets with good efficacy in cellular models of apoptosis, and they are useful for treating caspase-mediated diseases such as those described below.

DETAILED DESCRIPTION OF THE INVENTION

This invention provides novel compounds, and pharmaceutically acceptable derivatives thereof, that are useful as caspase inhibitors. The invention also provides methods for using the compounds to inhibit caspase activity and to treat caspase-mediated disease states in mammals. These compounds have the general formula I:

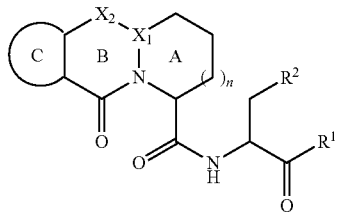

wherein:
$R^1$ is hydrogen, $CHN_2$, R, or —$CH_2Y$;
R is an aliphatic group, an aryl group, an aralkyl group, a heterocyclic group, or a heterocyclylalkyl group;
Y is an electronegative leaving group;
$R^2$ is $CO_2H$, $CH_2CO_2H$, or esters, amides or isosteres thereof;
$X_2$—$X_1$ is $N(R^3)$—$C(R^3)$, $C(R^3)_2$—$C(R^3)$, $C(R^3)_2$—N, N=C, $C(R^3)$=N, $C(R^3)$=C, C(=O)—N, or C(=O)—C $(R^3)$;
each $R^3$ is independently selected from hydrogen or a $C_{1-6}$ aliphatic group,
Ring C is a fused aryl ring;
n is 0, 1 or 2; and
each methylene carbon in Ring A is optionally and independently substituted by =O, or by one or more halogen, $C_{1-4}$ alkyl, or $C_{1-4}$ alkoxy.

As used herein, the following definitions shall apply unless otherwise indicated:

The term "aliphatic" as used herein means straight chained or branched $C_1$-$C_{12}$ hydrocarbons which are completely saturated or which contain one or more units of unsaturation. Aliphatic groups include substituted or unsubstituted linear, branched or cyclic alkyl, alkenyl, or alkynyl groups and hybrids thereof such as (cycloalkyl)alkyl, (cycloalkenyl)alkyl or (cycloalkyl)alkenyl. The term "alkyl" used alone or as part of a group or larger moiety refers to both straight and branched chains containing one to twelve carbon atoms. The term "halogen" means F, Cl, Br, or I.

The term "aryl" refers to monocyclic or polycyclic aromatic groups, and monocyclic or polycyclic heteroaromatic groups containing one or more heteroatoms, having five to fourteen atoms. Such groups include, but are not restricted to phenyl, naphthyl, anthryl, furanyl, thienyl, pyrrolyl, oxazolyl, triazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, tetrahydrofuranyl, phthalimidinyl, tetrazolyl, and chromanyl.

The term "heterocyclic group" refers to saturated and unsaturated monocyclic or polycyclic ring systems containing one or more heteroatoms and a ring size of three to eight. Such groups include, but are not restricted to aziranyl, oxiranyl, azetidinyl, tetrahydrofuranyl, pyrrolinyl, pyrrolidinyl, dioxolanyl, imidazolinyl, imidazolidinyl, pyrazolinyl, pyrazolidinyl, pyranyl, piperidinyl, dioxanyl, morpholinyl, dithianyl, thiomorpholinyl, piperazinyl, trithianyl, quinuclidinyl, oxepanyl, and thiepanyl.

The term "carbocyclic group" refers to saturated monocyclic or polycyclic carbon ring systems which may be fused to aryl or heterocyclic groups. Examples could include cyclohexyl, cyclopentyl, cyclobutyl, cyclopropyl, indanyl, tetrahydronaphthyl and the like.

An aliphatic, alkyl, aryl, a heterocyclic, or a carbocyclic group may contain one or more substituents. Examples of suitable substituents include a halogen, —R, —OR, —OH, —SH, —SR, protected OH (such as acyloxy), phenyl (Ph), substituted Ph, —OPh, substituted —OPh, —$NO_2$, —CN, —$NH_2$, —NHR, —$N(R)_2$, —NHCOR, —NHCONHR, —$NHCON(R)_2$, —NRCOR, —$NHCO_2R$, —$CO_2R$, —$CO_2H$, —COR, —CONHR, —$CON(R)_2$, —$S(O)_2R$, —$SONH_2$, —S(O)R, —$SO_2NHR$, —$NHS(O)_2R$, =O, =S, =NNHR, =$NNR_2$, =N—OR, =NNHCOR, =$NNHCO_2R$, =$NNHSO_2R$, or =NR where R is an aliphatic group or a substituted aliphatic group.

A substitutable nitrogen on a heterocyclic ring may be optionally substituted. Suitable substituents on the nitrogen include R, COR, $S(O)_2R$, and $CO_2R$, where R is an aliphatic group or a substituted aliphatic group.

Nitrogen and sulfur may be in their oxidized form, and nitrogen may be in a quaternized form.

The term "electronegative leaving group" has the definition known to those skilled in the art (see March, *Advanced Organic Chemistry*, $4^{th}$ Edition, John Wiley & Sons, 1992). Examples of electronegative leaving groups include halogens such as F, Cl, Br, I, aryl- and alkylsulfonyloxy groups, trifluoromethanesulfonyloxy, OR, SR, —OC=O(R), —OPO $(R^3)(R^4)$, where R is an aliphatic group, an aryl group, an aralkyl group, a carbocyclic group, an alkyl carbocyclic group, a heterocyclic group, or an alkyl heterocyclic group; and $R^3$ and $R^4$ are independently selected from R or OR.

When the $R^2$ group is in the form of an ester or amide, the present compounds undergo metabolic cleavage to the corresponding carboxylic acids, which are the active caspase inhibitors. Because they undergo metabolic cleavage, the precise nature of the ester or amide group is not critical to the working of this invention. The structure of the $R^2$ group may range from the relatively simple diethyl amide to a steroidal ester. Examples of esters of $R^2$ carboxylic acids include, but are not limited to, $C_{1-12}$ aliphatic, such as $C_{1-6}$ alkyl or $C_{3-10}$ cycloalkyl, aryl, such as phenyl, aralkyl, such as benzyl or phenethyl, heterocyclyl or heterocyclylalkyl. Examples of suitable $R^2$ heterocyclyl rings include, but are not limited to, 5-6 membered heterocyclic rings having one or two heteroatoms such as piperidinyl, piperazinyl, or morpholinyl.

Amides of $R^2$ carboxylic acids may be primary, secondary or tertiary. Suitable substituents on the amide nitrogen include, but are not limited to, one or more groups independently selected from the aliphatic, aryl, aralkyl, heterocyclyl or heterocyclylalkyl groups described above for the $R^2$ ester alcohol. Likewise, other prodrugs are included within the scope of this invention. See Bradley D. Anderson, "Prodrugs for Improved CNS Delivery" in Advanced Drug Delivery Reviews (1996), 19, 171-202.

Isosteres or bioisosteres of $R^2$ carboxylic acids, esters and amides result from the exchange of an atom or group of atoms to create a new compound with similar biological properties to the parent carboxylic acid or ester. The bioisosteric replacement may be physicochemically or topologically based. An example of an isosteric replacement for a carboxylic acid is $CONHSO_2$(alkyl) such as $CONHSO_2Me$.

Compounds of this invention where $R^2$ is $CO_2H$ or $CH_2CO_2H$, γ-ketoacids or δ-ketoacids respectively, may exist in solution as either the open form 1 or the cyclized hemiketal form 2 (y=1 for γ-ketoacids, y=2 for δ-ketoacids). The representation herein of either isomeric form is meant to include the other.

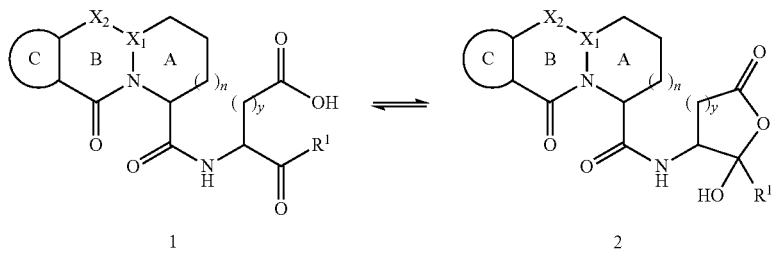

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

The compounds of this invention have inhibition properties across a range of caspase targets with good efficacy in cellular models of apoptosis. In addition, these compounds are expected to have good cell penetration and pharmacokinetic properties and, as a consequence of their potency, have good efficacy against diseases where caspases are implicated.

Ring C is preferably a fused five- or six-membered aryl ring having zero to two ring heteroatoms selected from oxygen, sulfur or nitrogen. More preferably Ring C is a fused six-membered aryl ring such as benzene or a ring where the atom adjacent to the Ring B/Ring C ring junction proximal to the Ring B carbonyl is an unsubstituted carbon. Ring C may be substituted or unsubstituted. Suitable Ring C substituents include halogen, —R, —OR, —OH, —SH, —SR, protected OH (such as acyloxy), phenyl (Ph), substituted Ph, —OPh, substituted —OPh, —NO$_2$, —CN, —NH$_2$, —NHR, —N(R)$_2$, —NHCOR, —NHCONHR, —NHCON(R)$_2$, —NR-COR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, —NHS(O)$_2$R, =O, =S, =NNHR, =NNR$_2$, =N—OR, =NNHCOR, =NNHCO$_2$R, =NNHSO$_2$R, or =NR where R is an aliphatic group or a substituted aliphatic group.

Preferred compounds of this invention are compounds of formula I that have one or more of the following features, and more preferably all of the following features:

(a) $R^1$ is —CH$_2$Y wherein Y is a halogen, OR, SR, or —OC=O(R), wherein R is an aryl group or heterocyclic group;
(b) $R^2$ is CO$_2$H or esters, amides or isosteres thereof;
(c) $X_2$—$X_1$ is N=C, C(R$^3$)=C, or C(=O)—N;
(d) Ring C is a fused five or six-membered aromatic ring having zero to two heteroatoms; and/or
(e) n is 0 or 1, wherein $R^3$ is as described above. Preferably, $R^3$ is a $C_{1-6}$ alkyl group.

Most preferred compounds of this invention are compounds of formula I that have the following features:

(a) $R^1$ is —CH$_2$Y wherein Y is F;
(b) $R^2$ is CO$_2$H or an ester thereof;
(c) $X_2$—$X_1$ is N=C, CH=C, or C(=O)—N;
(d) Ring C is a benzene or pyrazine ring; and
(e) n is 0 or 1.

Representative tricyclic ring systems of formula I include, but are not limited to, those provided in Table 1. For illustrative purposes, Ring C is shown as a benzo-fused ring, and not all of the possible R$^3$ substituents are shown. Table 2 that follows shows specific representative examples of formula I compounds.

TABLE 1

Examples of Tricyclic Systems of Formula I where Ring C is a benzo-fused ring

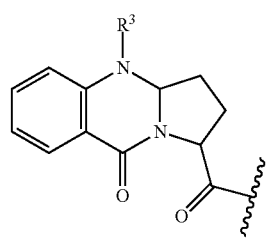

a

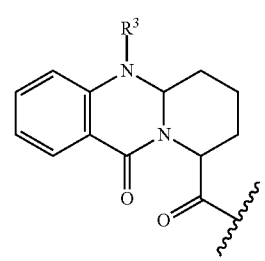

b

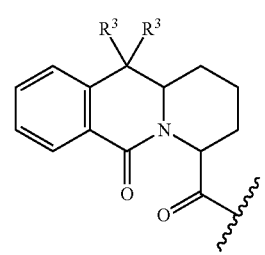

c

TABLE 1-continued
Examples of Tricyclic Systems of Formula I
where Ring C is a benzo-fused ring
d
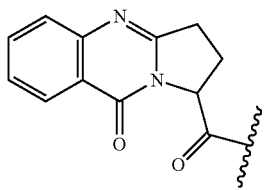
e
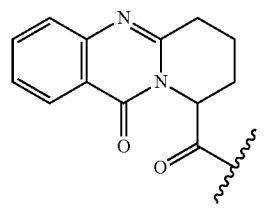
f
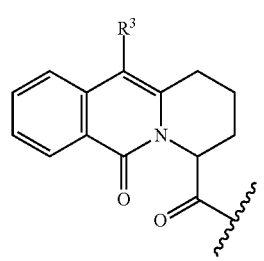
g
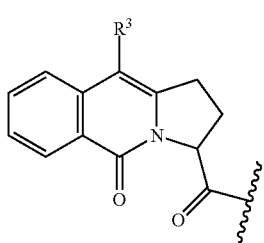
h
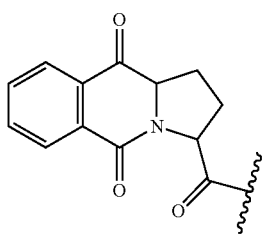
i
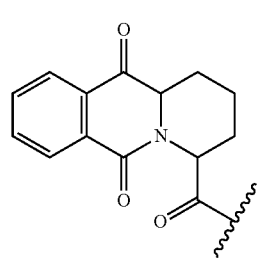
TABLE 1-continued
Examples of Tricyclic Systems of Formula I
where Ring C is a benzo-fused ring
j
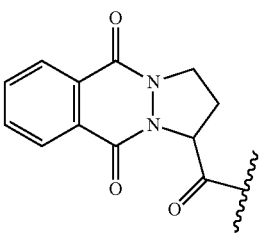
k
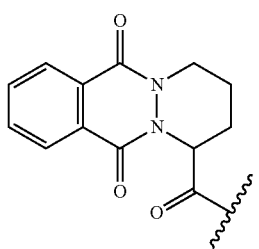
l
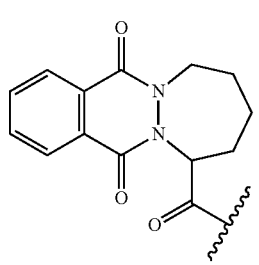
m
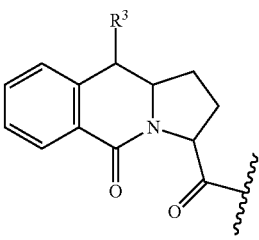
n
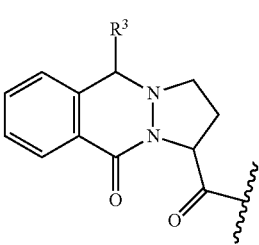

TABLE 1-continued

Examples of Tricyclic Systems of Formula I
where Ring C is a benzo-fused ring o
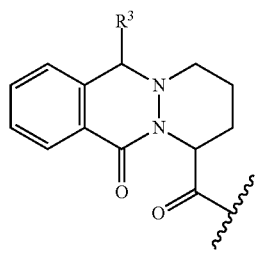

p
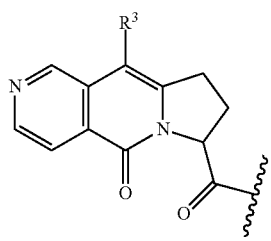

q
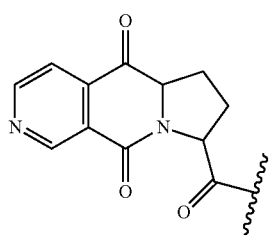

r
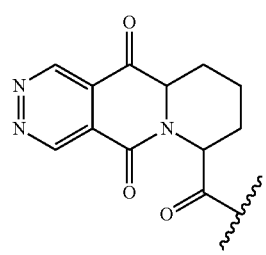

s
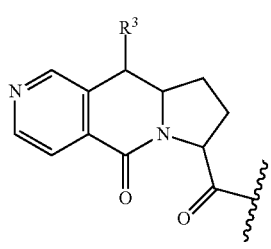

TABLE 1-continued

Examples of Tricyclic Systems of Formula I
where Ring C is a benzo-fused ring t
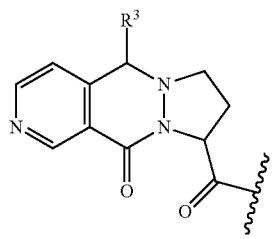

u
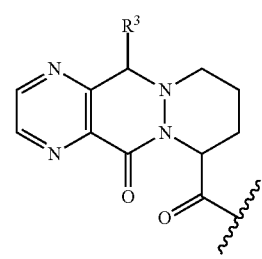

v
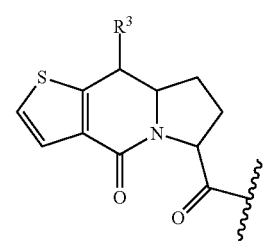

TABLE 2

Examples of Formula I compounds

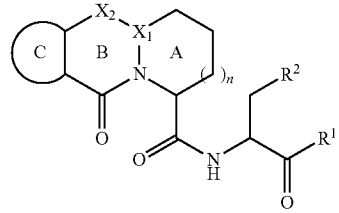

| Example | $R^1$ | $R^2$ | Ring C | n | $X_1$ | $X_2$ |
|---------|-------|-------|--------|---|-------|-------|
| 1 | $CH_2F$ | $CO_2H$ | benzo | 0 | C | N |
| 2 | $CH_2F$ | $CO_2H$ | benzo | 1 | C | N |
| 3 | $CH_2F$ | $CO_2H$ | benzo | 0 | C | C—H |
| 4 | $CH_2F$ | $CO_2H$ | benzo | 1 | C | C—H |
| 5 | $CH_2F$ | $CO_2H$ | benzo | 1 | N | C═O |
| 6 | $CH_2F$ | $CO_2H$ | pyrazino | 1 | N | C═O |

The compounds of this invention may be prepared in general by methods known to those skilled in the art for analogous compounds, as illustrated by the general Scheme I below and by the preparative examples that follow.

Scheme I

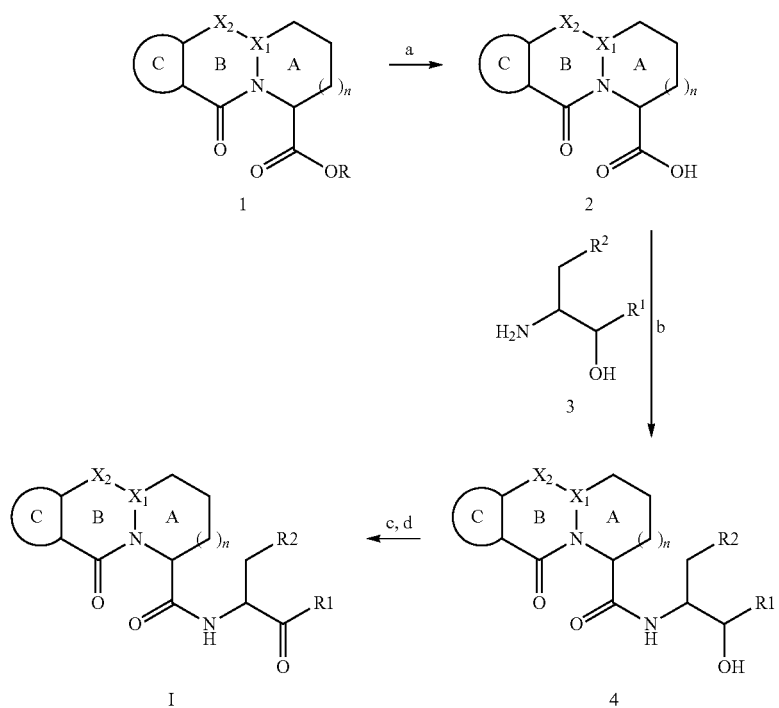

Reagents: (a) TFA or KOH/MeOH; (b) EDC/DMAP/HOBt; (c) Dess-Martin periodinane; (d) TFA/DCM Tricyclic ring system 1 is generally prepared as an ester (see Schemes 2-4). Ester 1 (R is any suitable organic radical) is first hydrolyzed using base or, when the ester is a t-butyl group, using trifluoroacetic acid. The acid 2 is then coupled with the amino alcohol 3. Depending on the nature of $R^1$ and $R^2$ an amino ketone may be used, in place of the amino alcohol, which avoids the subsequent oxidation step. In the case of fluoromethyl ketones where $R^1$ is $CH_2F$, the amino alcohol 3 may be obtained according to the method of Revesz et al., *Tetrahedron Lett.*, 1994, 35, 9693. Finally the hydroxyl in compound 4 is oxidized and the compound treated appropriately according to the nature of $R^2$. For example, if the product I requires $R^2$ to be a carboxylic acid, then $R^2$ in 3 is preferably an ester and the final step in the scheme is hydrolysis (alternatively if the ester is a tert-butyl ester, the final step is treatment with trifluoroacetic acid).

The parent tricyclic esters 1 may be prepared as outlined in Schemes II, III and IV for 1a, 1b and 1c respectively, as shown below.

Scheme II

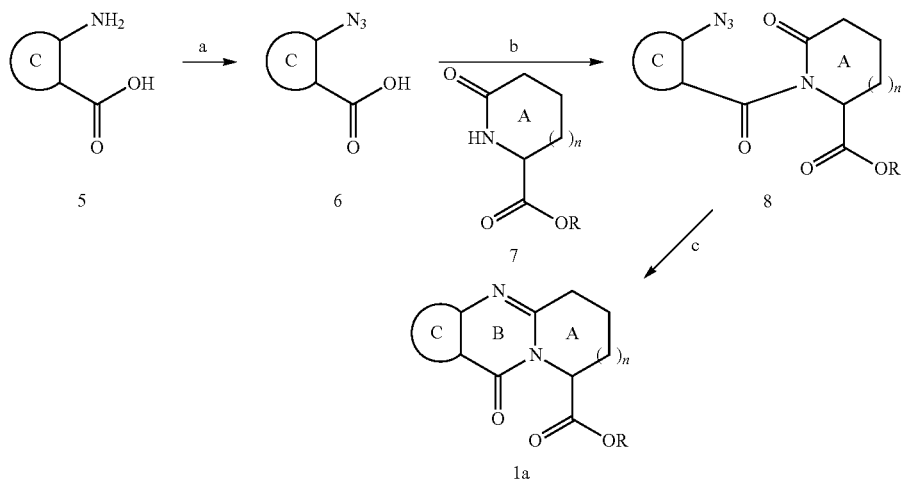

Details: (a) $NaNO_2/HCl$, $NaN_3/AcONa$; (b) $SOCl_2$, lithium anion of lactam 7; (c) $PPh_3$/xylene.

The tricyclic esters 1a where $X_2$—$X_1$ is N═C, can be prepared as outlined in Scheme II. The starting aminoacid 5 is first converted into the diazonium salt, and then treated with sodium azide in aqueous sodium acetate to give the azidoacid 6. The azidoacid 6 is then coupled to the lactam 7 by condensation of the acid chloride of 6 (prepared in situ from reaction of 6 with thionyl chloride), with the lithium salt of lactam 7 (prepared by reaction of LDA with 7) to give 8. Intramolecular aza-Wittig reaction of 8, using triphenylphosphine and refluxing xylene, affords the tricyclic esters 1a.

The tricyclic esters 1b, where $X_1$ and $X_2$ are both carbon, can be prepared as outlined in Scheme III.

-continued

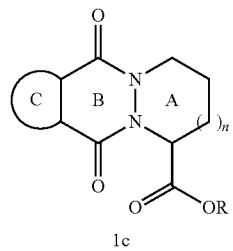

Reagents: (a) diisopropylethylamine, toluene.

Scheme III

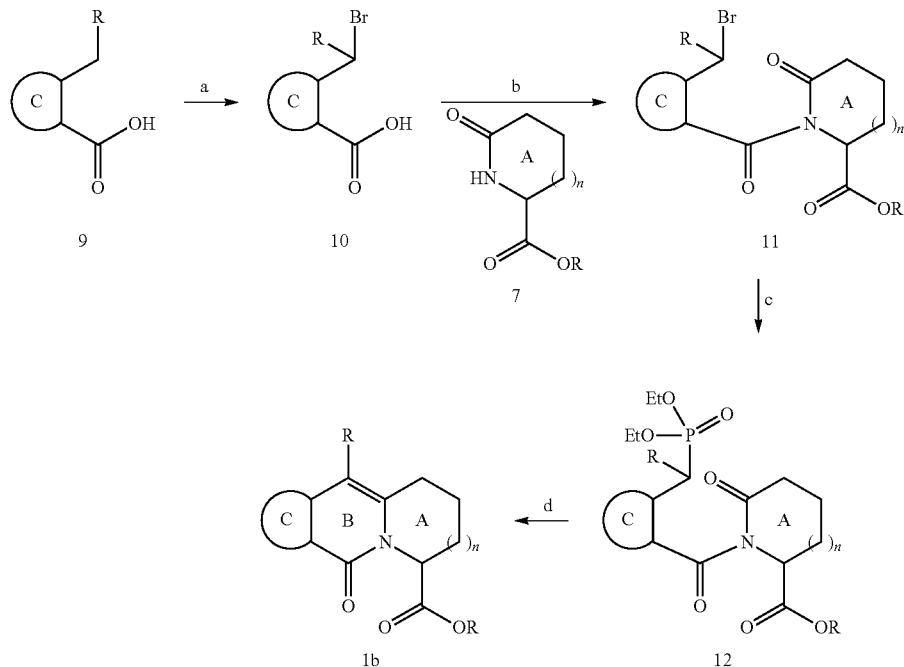

Details: (a) NBS, chloroform; (b) SOCl$_2$, lithium anion of lactam 7; (c) P(OEt)$_3$; (d) LHMDS, THF.

The starting ortho substituted aromatic acid 9 is first brominated (NBS in chloroform) to provide bromide 10. The acid chloride of 10 (prepared by reaction of 10 with thionyl chloride) is then reacted with the lithium salt of lactam 7 (prepared by reaction of LDA with lactam 7) to give 11. Reaction of 11 with triethylphosphite provides 12, which undergoes an intramolecular Wittig-Horner reaction in the presence of a base in THF to afford tricyclic esters 1b.

Scheme IV

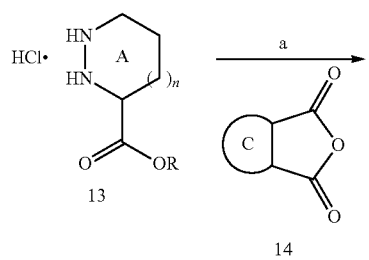

The tricyclic esters 1c, where $X_2$—$X_1$ is C(═O)—N, can be prepared by reaction of heterocyclic esters of the type 13 with aromatic anhydrides 14, as outlined in Scheme IV above.

The parent heterocyclic esters 7 and 13 used in Schemes II, III and IV, or their acids or derivatives, are either commercially available or can be prepared using standard methods. The parent heterocyclic acid 7, where n is zero, is commercially available (pyroglutamic acid). In addition, pyroglutamic acid can be substituted at position 4 using various electrophiles, according standard methods (J. Ezquerra et al., Tetrahedron, 1993, 49, 8665-8678; J. D. Charrier et al., Tetrahedron Lett., 1998, 39, 2199-2202). The parent heterocyclic ester 7, where n is one, can be prepared according to the procedures described in the experimental section below. The parent heterocyclic acid 7, where n is two, can be prepared by standard methods (Perrotti et al., Ann. Chim (Rome), 1966, 56, 1368). The parent heterocyclic esters 13 where n is zero can be prepared by literature methods (M. R. Mish et al., J. Am. Chem. Soc., 1997, 119, 35, 8379-8380); and the parent heterocyclic esters 13 where n is one also can be prepared by literature methods (Y. Nakamura et al., Chem. Lett., 1991, 11, 1953-1956).

The compounds of this invention are designed to inhibit caspases. Therefore, the compounds of this invention can be assayed for their ability to inhibit apoptosis, the release of IL-1β or caspase activity directly. Assays for each of the activities are known in the art and are described below in detail in the Testing section.

One embodiment of this invention relates to a composition comprising a compound of formula I or a pharmaceutically acceptable derivative thereof, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, apoptosis mediated disease, an inflammatory disease, autoimmune disease, destructive bone disorder, proliferative disorder, infectious disease, degenerative disease, disease associated with cell death, excess dietary alcohol intake disease, and viral mediated disease. Such diseases include uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polyaptic kidney disease, *H. pylori*-associated gastric and duodenal ulcer disease, HIV infection, tuberculosis, and meningitis. The compounds and compositions are also useful in treating complications associated with coronary artery bypass grafts and as a component of immunotherapy for the treatment of various forms of cancer.

The amount of compound present in the above-described compositions should be sufficient to cause a detectable decrease in the severity of the disease or in caspase activity and/or cell apoptosis, as measured by any of the assays described in the examples.

The compounds of this invention are also useful in methods for preserving cells, such as may be needed for an organ transplant or for preserving blood products. Similar uses for caspase inhibitors have been reported (Schierle et al., *Nature Medicine*, 1999, 5, 97). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

EXPERIMENTAL

In the following Examples, $^{19}$F NMR are $^1$H decoupled and all peaks are singlets unless otherwise stated.

Example 1

[3S/R(1S)]-3-(2,3-Dihydro-1H-9-oxo-pyrrolo[2,1-b]quinazolin-1-carboxamido)-5-fluoro-4-oxo-pentanoic acid

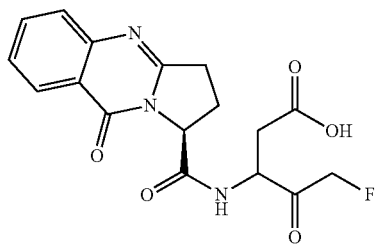

Method A (S)-1-(2-Azido-benzoyl)-5-oxo-pyrrolidine-2-carboxylic acid tert-butyl ester

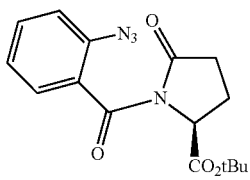

A stirred solution of (2S)-5-oxo-proline tert-butyl ester (T. Kolasa and M. J. Miller, J. Org. Chem., 1990, 55, 1711-1721) (1.13 g, 6.13 mmol) in anhydrous THF (15 mL) was treated at −78° C. with LDA (9.19 mmol) and the reaction was stirred for 15 min. A solution of 2-azidobenzoyl chloride (T. Okawa, T. Sugimori, S. Eguchi and A. Kakehi, Heterocycles, 1998, 47, 1, 375-382) (6.13 mmol) in anhydrous THF (5 mL) was then added dropwise and the reaction mixture was stirred at −78° C. for 1 h before being quenched with saturated aq.NH$_4$Cl. The reaction was allowed to warm to room temperature and the organic layer was washed with saturated aq.NH$_4$Cl, dried (MgSO$_4$), filtered and evaporated to give an oil which was purified by flash chromatography (20% ethyl acetate in hexane) to afford the title compound as a pale yellow oil (1.67 g, 82%): $^1$H NMR (400 MHz, CDCl$_3$) δ 1.53 (9H, s), 2.14 (1H, m), 2.43 (1H, m), 2.55 (1H, m), 2.69 (1H, m), 4.79 (1H, dd, J 9.2, 3.2 Hz), 7.19-7.22 (2H, m), 7.36 (1H, m), 7.49 (1H, m). $^{13}$C NMR (100 MHz, CDCl$_3$) δ 22.1 (CH$_2$), 28.3 (CH$_3$), 31.9 (CH$_2$), 59.3 (CH), 83.0 (C), 118.7 (CH), 125.0 (CH), 127.9 (C), 129.1 (CH), 131.9 (CH), 137.9 (C), 167.5 (C), 170.2 (C), 173.6 (C).

Method B:

(S)-2,3-Dihydro-1H-9-oxo-pyrrolo[2,1-b]quinazolin-1-carboxylic acid tert-butyl ester

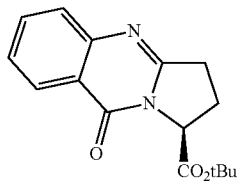

Triphenylphosphine (1.19 g, 4.54 mmol) was added portionwise to a solution of (3S/R)-5-fluoro-4-oxo-3-[((S)-9-oxo-1,2,3,9-tetrahydro-pyrrolo[2,1-b]quinazoline-1-carbonyl)-amino]-pentanoic acid (1.36 g, 4.12 mmol) in xylene (60 mL) at room temperature. The reaction mixture was stirred at room temperature until the evolution of nitrogen ceased (approx. 1 h), and then refluxed for 20 h. The volatiles were evaporated and the residue was purified by flash chromatography (50% ethyl acetate in hexane) to afford the title compound as a colourless oil (1.05 g, 89%): $^1$H NMR (400 MHz, CDCl3) δ 1.44 (9H, s), 2.26 (1H, m), 2.51 (1H, m), 3.06 (1H, m), 3.20 (1H, m), 4.99 (1H, dd, J 9.5, 2.8 Hz), 7.39 (1H, m), 7.59 (1H, m), 7.68 (1H, m), 8.21 (1H, m). $^{13}$C NMR (100 MHz, CDCl$_3$) δ 24.6 (CH$_2$), 28.3 (CH$_3$), 31.5 (CH$_2$), 60.4 (CH), 83.3 (C), 120.9 (C), 126.7 (CH), 126.9 (CH), 127.2 (CH), 134.7 (CH), 149.5 (C), 159.4 (C), 160.8 (C), 169.3 (C).

Method C (S)-2,3-Dihydro-1H-9-oxo-pyrrolo[2,1-b]quinazolin-1-carboxylic acid

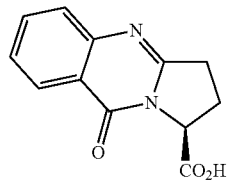

A solution of (1S)-9-oxo-1,2,3,9-tetrahydro-pyrrolo[2,1-b]quinazoline-1-carboxylic acid tert-butyl ester (1.01 g, 3.53 mmol) in TFA (20 mL) was stirred at room temperature for 4 h. The mixture was concentrated under reduced pressure and the residue was dissolved in dry DCM. This process was repeated several times to remove excess TFA. The gum was triturated with diethyl ether, filtrated and washed several times with diethyl ether to afford the title compound as a white powder (620 mg, 76%): $^1$H NMR (400 MHz, CD$_3$OD) δ 2.40 (1H, m), 2.71 (1H, m), 3.19 (1H, m), 3.27 (1H, m), 4.91

(exchangeable H), 5.19 (1H, dd, J 9.8, 2.8 Hz), 7.53 (1H, m), 7.69 (1H, m), 7.85 (1H, m), 8.23 (1H, m).

Method D

[3S/R, 4S/R, (1S)]-3-(2,3-Dihydro-1H-9-oxo-pyrrolo [2,1-b]quinazolin-1-carboxamido)-5-fluoro-4-hydroxy-pentanoic acid tert-butyl ester

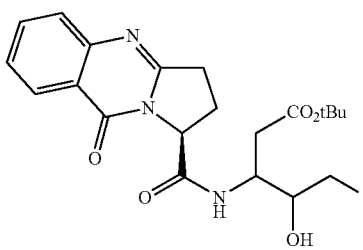

A mixture of (S)-9-oxo-1,2,3,9-tetrahydro-pyrrolo[2,1-b] quinazoline-1-carboxylic acid (0.10 g, 0.434 mmol), 3-amino-5-fluoro-4-hydroxy-pentanoic acid tert-butyl ester (0.099 g, 0.48 mmol), HOBt (0.065 g, 0.48 mmol), and DMAP (0.058 g, 0.48 mmol) in anhydrous THF (7 mL) was treated with EDC (0.092 g, 0.48 mmol) at 0° C. with stirring. The reaction mixture was allowed to warm to room temperature over 18 h, after which it was concentrated under reduced pressure to give a gum. This was purified by flash chromatography (EtOAc) to afford the title compound as a white powder (155 mg, 85%): $^1$H NMR (400 MHz, DMSO-d$_6$) δ 1.41 (9H, m), 1.99-3.07 (6H, m), 3.53-4.55 (4H, m), 4.91-5.12 (1H, m), 5.37-5.62 (1H, m), 7.42 (1H, m), 7.63 (1H, m), 7.80 (1H, m), 8.08 (1H, m), 8.29-8.57 (1H, m); $^{19}$F NMR (376 MHz, DMSO-d$_6$) δ −226.5, −226.5, −226.7, −226.7, −227.9, −228.0, −229.0, −229.0.

Method E

[3S/R, (1S)]-3-(2,3-Dihydro-1H-9-oxo-pyrrolo[2,1-b]quinazolin-1-carboxamido)-5-fluoro-4-oxo-pentanoic acid tert-butyl ester

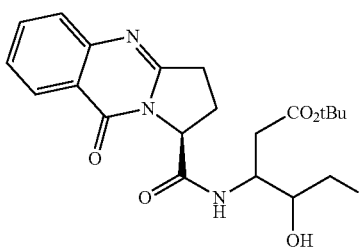

A solution of [3S/R(1S)]-5-fluoro-4-hydroxy-3-(9-oxo-1,2, 3,9-tetrahydro-pyrrolo[2,1-b]quinazoline-1-carboxamido)-pentanoic acid tert-butyl ester (0.147 g, 0.35 mmol) in anhydrous DCM (7 mL) was treated with 1,1,1-triacetoxy-1,1-dihydro-1,2-benziodoxol-3(1H)-one (0.297 g, 0.70 mmol) with stirring at 0° C. The reaction mixture was allowed to warm to room temperature and stirred for 18 h after which it was diluted with DCM and washed sequentially with 10% aq. Na$_2$SO$_3$.5H$_2$O, saturated aq. NaHCO$_3$ and brine. The organic phase was dried (Na$_2$SO$_4$) and concentrated to give a gum. This was purified by flash chromatography (5% MeOH in DCM) to afford the title compound as a white solid (113 mg, 77%): $^1$H NMR (400 MHz, CDCl$_3$) δ 1.35-1.42 (9H, 2 s), 2.37-2.62 (2H, m), 2.76-2.82 (1H, m), 2.88-2.97 (1H, m), 3.05-3.12 (1H, m), 3.35-3.42 (1H, m), 4.85-5.30 (4H, m), 7.41-7.89 (4H, m), 8.19-8.23 (1H, m); $^{13}$C NMR (100 MHz, CDCl$_3$) 24.1/24.2 (CH$_2$), 28.2/28.3 (CH$_3$), 32.0 (CH$_2$), 36.6 (CH$_2$), 52.8/52.9 (CH), 60.8/60.8 (CH), 82.7/82.7 (C), 84.7/84.8 (CH$_2$F), 120.0 (C), 126.8 (CH), 126.9/127.0 (CH), 127.4 (CH), 135.1 (CH), 149.4/149.5 (C), 159.5 (C), 161.5/161.6 (C), 169.4/169.7 (C), 170.2/170.3 (C), 202.6/202.8 (C); $^{19}$F NMR (376 MHz, CDCl$_3$) δ −231.9, −232.5.

Method F:

[3S/R(1S)]-3-(2,3-Dihydro-1H-9-oxo-pyrrolo[2,1-b] quinazolin-1-carboxamido)-5-fluoro-4-oxo-pentanoic acid

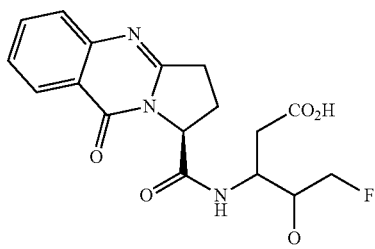

TFA (4 mL) was added to a stirred ice cold solution of [3S/R(1S)]-5-fluoro-4-oxo-3-(9-oxo-1,2,3,9-tetrahydro-pyrrolo [2,1-b]quinazoline-1-carboxamido)-pentanoic acid tert-butyl ester (80 mg, 0.19 mmol) in anhydrous DCM (4 mL). The mixture was stirred at 0° C. for 0.5 h then at room temperature for 0.5 h. The mixture was concentrated under reduced pressure and then the residue was dissolved in dry DCM. This process was repeated several times in order to remove excess TFA. The gum was triturated with diethyl ether and the resulting solid collected by filtrated. The solid was washed several times with diethyl ether to afford the title compound as a white solid (65 mg, 94%): IR (solid) 2366, 1793, 1675, 1557, 1194, 1137 cm$^{-1}$; $^1$H NMR (400 MHz, DMSO-d$_6$) δ 2.04-2.13 (1H, m), 2.48-3.18 (5H, m), 4.33-5.42 (4H, m), 7.50 (1H, m), 7.64 (1H, m), 7.82 (1H, m), 8.10 (1H, m), 9.06-9.14 (1H, m), 12.61 (1H, br s); $^{13}$C NMR (100 MHz, DMSO-d$_6$) δ 24.2/24.3 (CH$_2$), 31.0/31.1 (CH$_2$), 34.6/34.8 (CH$_2$), 52.1/52.6 (CH), 60.0/60.3 (CH), 84.3/84.4 (2×d, J 177.9, 177.7 Hz, CH$_2$F), 120.47 (C), 126.2 (CH), 126.5 (CH), 127.0 (CH), 134.9 (CH), 149.3 (C), 149.3 (C), 160.1 (C), 160.7/160.8 (C), 170.6 (C), 172.1/172.2 (C), 202.4/202.7 (2×d, J 14.0, 14.0 Hz, CO); $^{19}$F NMR (376 MHz, DMSO-d$_6$) δ −226.6 (t), −226.9 (t), −230.2 (t), −231.6 (t), −233.0 (t), −233.1 (t), −75.5 (s, TFA, 1 eq); MS (FAB +ve, HR) calculated for C$_{17}$H$_{17}$N$_3$O$_5$F (MH+) 362.115224. Found 362.115448.

Example 2

[3S/R(9S)]-5-Fluoro-4-oxo-3-(11-oxo-6,7,8,9-tetrahydro-11H-pyrido[2,1-b]quinazolin-9-carboxamido)-pentanoic acid

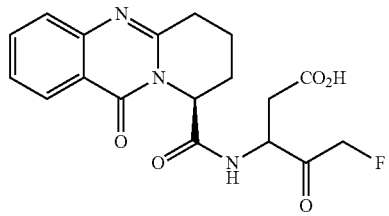

Method G:

(S)-Piperidine-1,2-dicarboxylic acid di-tert-butyl ester

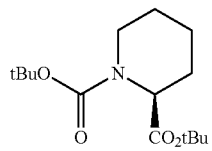

To a solution of (S)-piperidine-2-carboxylic acid tert-butyl ester (M. Egbertson and S. J. Danishefsky, J. Org. Chem., 1989, 54, 1, 11-12) (5.78 g, 31.2 mmol) in CH$_3$CN (30 mL) at 0° C. was added DMAP (763 mg, 6.2 mmol) followed by BOC$_2$O (10.22 g, 46.8 mmol). The reaction mixture was allowed to warm to room temperature and stirred for 20 h. The solvents were evaporated under reduced pressure and the residue was purified by flash chromatography (10% ethyl acetate in hexane). The title compound was obtained as a colourless oil which crystallized upon standing (8.33 g, 94%): $^1$H NMR (400 MHz, CDCl$_3$) δ 1.21-1.32 (2H, m), 1.47-1.48 (18H, 2 s), 1.59-1.72 (3H, m), 2.18 (1H, m), 2.85-3.00 (1H, m), 3.89-4.01 (1H, 2 d, J 11.9 Hz), 4.47-4.58 (1H, 2 br s).

Method H:

(S)-6-Oxo-piperidine-1,2-dicarboxylic acid di-tert-butyl ester

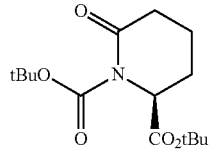

To a vigorously stirred solution of RuCl$_3$.H$_2$O (2.39 g, 11.5 mmol) and NaIO$_4$ (24.6 g, 115.0 mmol) in water (250 mL) was added (S)-piperidine-1,2-dicarboxylic acid di-tert-butyl ester (8.22 g, 28.8 mmol) in ethyl acetate (250 mL) at room temperature. After stirring for 4 h, the reaction mixture was partitioned and the aqueous layer washed with ethyl acetate. To the combined organic layers was added iPrOH (2.5 mL) and stirring was continued for 2 hours in order to destroy excess RuO$_4$. The precipitate was removed by filtration through a pad of celite and the filtrate was evaporated under reduced pressure. The residue was purified by flash chromatography (30% ethyl acetate in hexane) to afford the title compound as a pale yellow oil, which crystallized upon standing (6.69 g, 78%): $^1$H NMR (400 MHz, CDCl$_3$) δ 1.49 (9H, s), 1.52 (9H, s), 1.75-1.82 (2H, m), 1.97-2.06 (1H, m), 2.15-2.21 (1H, m), 2.41-2.61 (2H, m), 4.59 (1H, dd, J 3.5 Hz)

Method I:

(S)-6-Oxo-piperidine-2-carboxylic acid tert-butyl ester

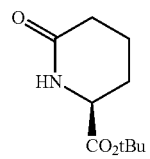

To a solution of (S)-6-oxo-piperidine-1,2-dicarboxylic acid di-tert-butyl ester (6.30 g, 21.0 mmol) in ethyl acetate (50 mL) was added 1.1-M HCl in ethyl acetate (28.7 mL, 31.5 mmol). The reaction was stirred at room temperature for 1 h, then washed with water, saturated aq.NaHCO$_3$ and brine. The organic phase was dried (MgSO$_4$), filtered and evaporated to afford the title compound as a yellow oil which crystallized upon standing (3.11 g, 74%): 1H NMR (400 MHz, CDCl3) δ 1.49 (9H, s), 1.74-1.94 (3H, m), 2.18 (1H, m), 2.29-2.44 (2H, m), 3.95-3.98 (1H, m), 6.32 (1H, br s); 13C NMR (100 MHz, CDCl3) δ 19.9 (CH$_2$), 25.9 (CH$_2$), 28.4 (CH$_3$), 31.4 (CH$_2$), 55.7 (CH), 83.0 (C), 170.4 (C), 171.9 (C).

[3S/R(9S)]-5-Fluoro-4-oxo-3-(11-oxo-6,7,8,9-tetrahydro-11H-pyrido[2,1-b]quinazolin-9-carboxamido)-pentanoic acid

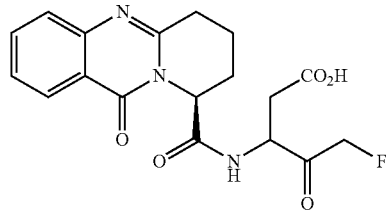

This was prepared from (S)-6-oxo-piperidine-2-carboxylic acid tert-butyl ester using procedures similar to those described in methods A-F. The product was isolated as a white solid (139 mg, 95%): IR (solid) 2361, 2342, 1727, 1665, 1560, 1198, 1126 cm$^{-1}$; $^1$H NMR (400 MHz, DMSO-d$_6$) 1.66-1.78 (2H, m), 2.14-2.17 (2H, m), 2.72 (2H, m), 2.92 (2H, m), 4.52-4.60 (1H, m), 4.80-5.30 (3H, m), 7.45-7.49 (1H, m), 7.58-7.60 (1H, m), 7.79-7.83 (1H, m), 8.06-8.09 (1H, m), 8.91 (1H, m), 12.51 (1H, br s); $^{13}$C NMR (100 MHz, DMSO-d$_6$) δ 16.6/16.7 (CH$_2$), 26.2/26.2 (CH$_2$), 31.7/31.8 (CH$_2$), 55.3/55.7 (CH), 120.2/120.2 (C), 126.4 (CH), 126.4 (CH), 126.4 (CH), 134.9 (CH), 147.5 (C), 155.2 (C), 161.8 (C), 171.2 (C); Signals for Asp moiety too broad to be detected in ¹H and ¹³C NMR; ¹⁹F NMR (376 MHz, DMSO-d₆) −233.0 (br).

Example 3

[3S/R(3S)]-3-(2,3-Dihydro-1H-5-oxo-pyrrolo[1,2-b]isoquinolin-3-carboxamido)-5-fluoro-4-oxo-pentanoic acid

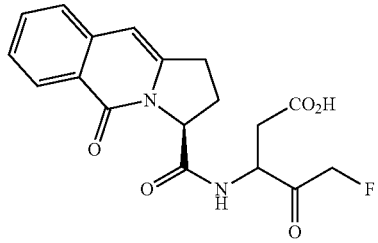

Method J:

(S)-1-(2-Bromomethylbenzoyl)-5-oxo-pyrrolidine-2-carboxylic acid tert-butyl ester

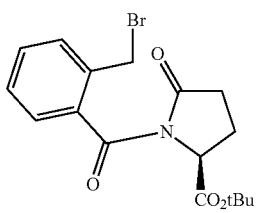

A stirred solution of α-bromotoluic acid (L. Garuti, A. Ferranti, M. Roberti, E. Katz, R. Budriesi and A. Chiarini, Pharmazie, 1992, 47, 295-297) (1.0 g, 4.7 mmol) in SOCl₂ (3.4 mL) was heated at 80° C. for 2 h. The solvent was evaporated and the residue dissolved in toluene. This process was repeated several times, to remove excess SOCl₂, and to eventually afford the desired acid chloride as a yellow oil. A stirred solution of (2S)-5-oxo-proline tert-butyl ester (T. Kolasa, and M. J. Miller, J. Org. Chem., 1990, 55, 1711-1721) (861 mg, 4.7 mmol) in anhydrous THF (15 mL) was treated at −78° C. with LDA (7.0 mmol) and the reaction was stirred for 15 min. A solution of the 2-α-bromotoluoyl chloride, prepared above, in anhydrous THF (5 mL) was then added dropwise and the reaction mixture was stirred at −78° C. for 1 h before being quenched with saturated aq.NH₄Cl. The reaction was allowed to warm to room temperature and partitioned. The organic layer was washed with saturated aq.NH₄Cl, dried (MgSO₄), filtered and evaporated to give an oil which was purified by flash chromatography (30% ethyl acetate in hexane) to afford the title compound as a pale yellow oil (1.46 g, 82%): ¹H NMR (400 MHz, CDCl₃) δ 1.55 (9H, s), 2.12-2.19 (1H, m), 2.38-2.59 (2H, m), 2.67-2.76 (1H, m), 4.54 (1H, d, J 10.5 Hz), 4.70 (1H, d, J 10.5 Hz), 4.86 (1H, dd, J 9.0, 3.7 Hz), 7.36-7.50 (4H, m). ¹³C NMR (100 MHz, CDCl₃) 22.0 (CH₂), 28.4 (CH₃), 30.5 (CH₂), 32.0 (CH₂), 59.2 (CH), 83.2 (C), 128.3 (CH), 128.4 (CH), 131.0 (CH), 131.0 (CH), 135.2 (C), 135.5 (C), 169.6 (C), 170.4 (C), 173.6 (C).

Method K:

(S)-1-[2-(Diethoxyphosphorylmethyl)benzoyl]-5-oxo-pyrrolidine-2-carboxylic acid tert-butyl ester

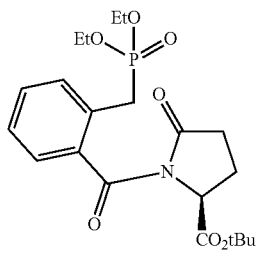

A mixture of (S)-1-(2-bromomethyl-benzoyl)-5-oxo-pyrrolidine-2-carboxylic acid tert-butyl ester (898 mg, 2.4 mmol) and triethylphosphite (432 mg, 2.4 mmol) was heated at 70° C. for 4 h. After cooling, the residue was purified by flash chromatography (ethyl acetate) to afford the title compound as a clear viscous oil (872 mg, 84%): ¹H NMR (400 MHz, CDCl₃) δ 1.17 (3H, t, J 7.0 Hz), 1.26 (3H, t, J 7.0 Hz), 1.53 (9H, s), 2.07-2.14 (1H, m), 2.43-2.69 (3H, m), 3.12 (1H, dd, J 22.4, 15.0 Hz), 3.62 (1H, dd, J 22.1, 15.0 Hz), 3.84-4.06 (4H, m), 4.87 (1H, dd, J 8.9, 4.8 Hz), 7.31-7.46 (4H, m).

Method L:

(S)-2,3-Dihydro-1H-5-oxo-pyrrolo[1,2-b]isoquinoline-3-carboxylic acid tert-butyl ester

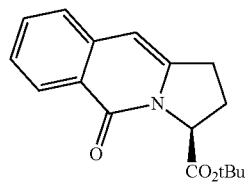

To a solution of (S)-1-[2-(diethoxyphosphorylmethyl)-benzoyl]-5-oxo-pyrrolidine-2-carboxylic acid tert-butyl ester (865 mg, 1.97 mmol) in THF (15 mL) at −40° C. was added drop-wise 1.0-M LHMDS in THF (1.97 mL, 1.97 mmol). The reaction mixture was stirred at −40° C. for 1 h, allowed to warm to 0° C. over 1 h, stirred at 0° C. for 1 h and allowed to warm to 7° C. over 30 min before being quenched with saturated aq.NH₄Cl. The reaction mixture was extracted with ethyl acetate (×2). The combined organic layers were dried (MgSO₄), filtered and evaporated. The residue was purified by flash chromatography (20% ethyl acetate in hexane) to afford the title compound as a colourless oil which crystallized upon standing (286 mg, 51%): ¹H NMR (400 MHz, CDCl₃) δ 1.47 (9H, s), 2.29 (1H, m), 2.47 (1H, m), 3.06 (1H, m), 3.19 (1H, m), 5.08 (1H, m), 6.42 (1H, s), 7.41-7.49 (2H, m), 7.63 (1H, m), 8.37 (1H, m); ¹³C NMR (100 MHz, CDCl₃) δ 25.8 (CH₂), 26.9 (CH₃), 28.7 (CH₂), 60.4 (CH), 81.3 (C), 99.3 (CH), 123.7 (C), 124.6 (CH×2), 126.5 (CH), 131.2 (CH), 137.3 (C), 142.4 (C), 160.2 (C), 168.7 (C).

[3S/R(3S)]-3-(2,3-Dihydro-1H-5-oxo-pyrrolo[1,2-b]isoquinolin-3-carboxamido)-5-fluoro-4-oxo-pentanoic acid

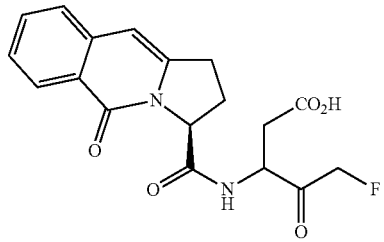

This was prepared from (S)-2,3-dihydro-(1H)-5-oxo-pyrrolo[1,2-b]isoquinoline-3-carboxylic acid tert-butyl ester using procedures similar to those described in methods C-F. The product was isolated as a white solid (102 mg, 89%): IR (solid) 2356, 1742, 1655, 1588, 1209 cm$^{-1}$; $^1$H NMR (400 MHz, DMSO-d$_6$) δ 2.07-2.12 (1H, m), 2.40-2.93 (3H, m), 3.07-3.18 (2H, m), 4.34-5.45 (4H, m), 6.56-6.57 (1H, 2 s), 7.41-7.45 (1H, m), 7.60-7.70 (2H, m), 8.11-8.16 (1H, m), 8.63-9.06 (1H, m), 12.49 (1H, br s); $^{13}$C NMR (100 MHz, DMSO-d$_6$) δ 26.7/26.8 (CH$_2$), 29.8/29.9 (CH$_2$), 34.6/34.9 (CH$_2$), 52.0/52.7 (CH), 61.4/61.7 (CH), 84.4/84.5 (2×d, J 177.7, 177.3 Hz, CH$_2$F), 99.6/99.7 (CH), 124.4/124.4 (C), 125.8 (CH), 126.2 (CH), 126.9 (CH), 127.0 (CH), 138.6 (C), 145.4/145.4 (C), 160.6 (C), 171.1/171.2 (C), 172.1/172.2 (C), 202.4/202.9 (CO); $^{19}$F NMR (376 MHz, DMSO-d$_6$) δ –226.6 (t), –226.9 (t), –233.1 (t), –233.3 (t); MS (FAB +ve, HR) calculated for C$_{18}$H$_{17}$N$_2$O$_5$F (MH+) 361.119975. Found 361.120247.

Example 4

[3S/R(4S)]-5-Fluoro-4-oxo-3-(6-oxo-1,2,3,4-tetrahydro-6H-benzo[b]quinolizin-4-carboxamido)-pentanoic acid

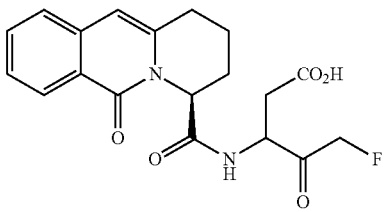

This was prepared from (S)-6-oxo-piperidine-2-carboxylic acid tert-butyl ester using procedures similar to those described in methods J-L and C-F. The product was isolated as a white solid (108 mg, 91%): IR (solid) 2361, 2337, 1736, 1641, 1365, 1217 cm$^{-1}$; $^1$H NMR (400 MHz, DMSO-d$_6$) δ 1.66 (2H, m), 2.08-2.13 (2H, m), 2.53-2.94 (4H, m), 4.29-4.69 (1H, m), 5.10-5.44 (3H, m), 6.43-6.46 (1H, m), 7.39-7.43 (1H, m), 7.54-7.56 (1H, m), 7.65-7.71 (1H, m), 8.09-8.14 (1H, m), 8.42-8.96 (1H, m, NH), 12.51 (1H, br s, OH); $^{13}$C NMR (100 MHz, DMSO-d$_6$) δ 16.7/16.8 (CH$_2$), 26.9/27.0 (CH$_2$), 28.9/29.0 (CH$_2$), 34.5/34.8 (CH$_2$), 52.1/52.8 (CH), 54.9/55.2 (CH), 84.3/84.5 (J 177.7, 177.1 Hz, CH$_2$F), 103.8/103.8 (CH), 123.9 (C), 125.5 (CH), 125.8 (CH), 127.3 (CH), 132.9 (CH), 137.1 (C), 141.0/141.1 (C), 162.7 (C), 172.1/172.2 (C), 172.2/172.3 (C), 202.6/203.1 (J 14.6, 13.8 Hz, CO); $^{19}$F NMR (376 MHz, DMSO-d$_6$) δ –226.6 (t), –226.9 (t), –233.2 (t), –233.4 (t).

Example 5

[3S/R(1S)]-3-(6,11-Dioxo-1,2,3,4-tetrahydro-pyridazino[1,2-b]phthalazin-1-carboxamido)-5-fluoro-4-oxo-pentanoic acid

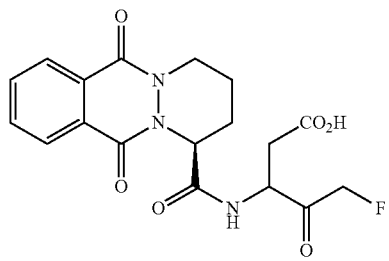

Method M:

(S)-6,11-Dioxo-1,2,3,4-tetrahydro-pyridazino[1,2-b]phthalazin-1-carboxylic acid methyl ester

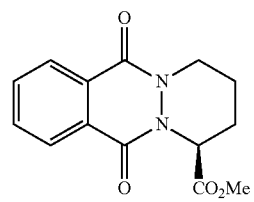

A solution of (S)-hexahydro-pyridazine-3-carboxylic acid methyl ester hydrochloride (Y. Nakamura, C. J Shin, Chem. Lett, 1991, 11, 1953-1956) (370 mg, 2.05 mmol), phthalic anhydride (318 mg, 2.15 mmol) and diisopropylethylamine (291 mg, 2.25 mmol) was heated in toluene (5 mL) for 2 h. The reaction mixture was then cooled and partitioned between ethyl acetate and dilute HCl. The organic phase was washed with saturated aq. NaHCO$_3$, dried (MgSO$_4$), filtered and evaporated. The residue was crystallised from hexane and filtered to afford the title compound as a white solid (562 mg, 82%): $^1$H NMR (400 MHz, CD$_3$OD) δ 1.59 (1H, m), 1.96 (1H, m), 2.17 (1H, m), 2.55 (1H, m), 3.38 (1H, m), 3.70 (3H, s), 4.89 (1H, m), 5.74 (1H, m), 7.89 (2H, m), 8.16 (2H, m). $^{13}$C NMR (100 MHz, CD$_3$OD) δ 21.2 (CH$_2$), 25.7 (CH$_2$), 46.0 (CH$_2$), 53.8 (CH), 58.1 (CH$_3$), 129.0 (CH), 129.1 (CH), 130.1 (C), 130.6 (C), 135.3 (CH), 135.7 (CH), 160.4 (C), 162.4 (C), 171.7 (C).

Method N:

(S)-6,11-Dioxo-1,2,3,4-tetrahydro-pyridazino[1,2-b]phthalazin-1-carboxylic acid

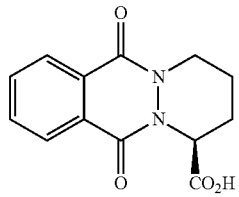

To a stirred solution of (S)-6,11-dioxo-1,2,3,4-tetrahydro-pyridazino[1,2-b]phthalazin-1-carboxylic acid methyl ester (1.078 g, 3.93 mmol) in MeOH (35 mL) was added KOH (232 mg, 4.12 mmol) in MeOH (11 mL) at 0° C. The reaction mixture was allowed to warm to room temperature and stirred for 20 hours, then concentrated under reduced pressure. The residue was dissolved in ethyl acetate and the resulting solution was extracted with water. The aqueous phase was acidified with 2.0-M HCl then extracted several times with ethyl acetate. The combined organic extracts were dried (MgSO$_4$), filtered and concentrated. The residue was crystallized from diethyl ether and the title compound was obtained as a white solid (744 mg, 73%): $^1$H NMR (400 MHz, CD$_3$OD) δ 1.80 (1H, m), 1.97 (1H, m), 2.16 (1H, m), 2.56 (1H, m), 3.36 (1H, m), 4.83-4.88 (2H, m), 5.71 (1H, m), 7.90 (2H, m), 8.26 (2H, m).

[3S/R(1S)]-3-(6,11-Dioxo-1,2,3,4-tetrahydro-pyridazino[1,2-b]phthalazin-1-carboxamido)-5-fluoro-4-oxo-pentanoic acid

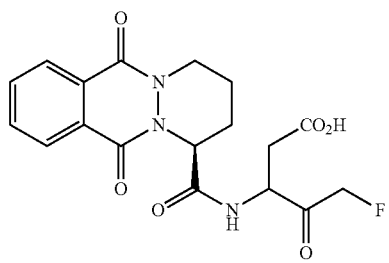

This was prepared from (S)-6,11-dioxo-1,2,3,4-tetrahydro-pyridazino[1,2-b]phthalazin-1-carboxylic acid using procedures similar to those described in methods D-F. The product was isolated as a white solid (349 mg, 85%): IR (solid) 2356, 2337, 1736, 1651, 1617, 1603, 1346, 1226, 1212 cm$^{-1}$; $^1$H NMR (400 MHz, DMSO-d$_6$) δ 1.62 (1H, m), 1.85 (1H, m), 2.11 (2H, m), 2.33 (1H, m), 2.70 (1H, m), 3.33 (1H, m), 4.54-4.96 (4H, m), 5.48 (1H, m), 7.87-7.94 (2H, m), 8.13-8.19 (2H, m), 8.72 (1H, m); $^{13}$C NMR (100 MHz, DMSO-d$_6$) (signals for Asp moiety not visible) δ 18.8 (2 peaks, CH$_2$), 24.9/24.1 (CH$_2$), 43.7 (CH$_2$), 56.7/56.8 (CH), 127.4/127.5 (CHar), 128.5 (2 peaks, Car), 129.2 (Car), 133.8/134.2 (CHar), 157.3 (CO), 159.4/159.6 (CO), 170.0 (CO); $^{19}$F NMR (376 MHz, DMSO-d$_6$+drop of TFA) δ −232.7, −232.8; MS (FAB +ve, HR) calculated for C$_{18}$H$_{18}$N$_3$O$_6$F (MH+) 392.125789. Found 392.125420.

Example 6

[3S/R(5S)]-(9,10-Dioxo-5,6,7,8,9,10-hexahydro-1,4,8a,10a-tetraazaanthracene-5-carboxamido)-5-fluoro-4-oxo-3-pentanoic acid

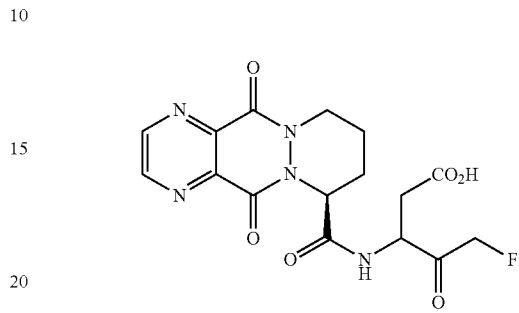

This was prepared from furo[3,4-b]pyrazine-5,7-dione using procedures similar to those described in methods M-N and D-F. The product was isolated as a white solid (150 mg, 90%): IR (solid) 1818, 1740, 1637, 1542, 1477, 1418, 1402, 1345, 1288, 1220, 1182, 1149, 1134, 1140, 1050, 934 cm$^{-1}$; $^1$H NMR (400 MHz, DMSO-d$_6$) δ 1.57 (1H, m), 1.85 (1H, m), 2.10 (1H, m), 2.50-2.95 (2H, m, Asp CH$_2$), 3.49 (1H, m), 4.22-4.72 (2.5H, m), 5.12 (1.5H, m); 5.46 and 5.55 (1H, 2×m), 8.85 (1H, m), 9.16 (2H, d); $^{13}$C NMR (100 MHz, DMSO-d$_6$) δ 18.8/19.1 (CH$_2$), 24.8/25.2 (CH$_2$), 32.9/33.1/34.5/34.6 (CH$_2$), 43.5/44.0/44.1 (Asp CH$_2$), 52.4/52.6 (CH), 57.3/57.4/57.6 (CH), 84.2/84.3 (J 178.5, 179.3 Hz, CH$_2$F), 140.9/141.0 (C), 141.5 (C), 149.9 (CH), 150.0/150.1 (CH), 156.2/156.3/156.3 (C), 158.4/158.4/158.8 (C), 169.4/169.5/169.8/169.8 (C), 172.0/173.1 (C=O), 202.4/202.5 (J 14.6, 14.3 Hz, C=O); $^{19}$F NMR (376 MHz, DMSO-d$_6$) δ −226.54 (t), −227.1 (t), −229.9 (t), −232.7 (t), −232.8 (t).

Example 7

Enzyme Assays

The assays for caspase inhibition are based on the cleavage of a fluorogenic substrate by recombinant, purified human Caspases -1, -3, -7 or -8. The assays are run in essentially the same way as those reported by Garcia-Calvo et al. (J. Biol. Chem. 273 (1998), 32608-32613), using a substrate specific for each enzyme. The substrate for Caspase-1 is Acetyl-Tyr-Val-Ala-Asp-amino-4-methylcoumarin. The substrate for Caspases -3, -7 and -8 is Acetyl-Asp-Glu-Val-Asp-amino-4-methylcoumarin.

The observed rate of enzyme inactivation at a particular inhibitor concentration, k$_{obs}$, is computed by direct fits of the data to the equation derived by Thornberry et al. (Biochemistry 33 (1994), 3943-3939) using a nonlinear least-squares analysis computer program (PRISM 2.0; GraphPad software). To obtain the second order rate constant, k$_{inact}$, k$_{obs}$ values are plotted against their respective inhibitor concentrations and k$_{inact}$ values are subsequently calculated by computerized linear regression.

Table 3 below shows inhibition of caspase-1 activity for a selected compound of this invention as determined by the above method.

TABLE 3

| Caspase-1 Activity | |
| --- | --- |
| Example Number | Kinact (M$^{-1}$s$^{-1}$) |
| 2 | 455000 |

Table 4 below shows inhibition of caspase-3 activity for a selected compound of this invention as determined by the above method.

TABLE 4

| Caspase-3 Activity | |
| --- | --- |
| Example Number | Kinact (M$^{-1}$s$^{-1}$) |
| 1 | 160500 |

Table 5 below shows inhibition of caspase-7 for a selected compound of this invention as determined by the above methods.

TABLE 5

| Caspase-7 Activity | |
| --- | --- |
| Example Number | Kinact (M$^{-1}$s$^{-1}$) |
| 3 | 229000 |

Table 6 below shows inhibition of caspase-8 activity for a selected compound of this invention as determined by the above methods.

TABLE 6

| Caspase-8 Activity | |
| --- | --- |
| Example Number | Caspase-8 Kinact (M$^{-1}$s$^{-1}$) |
| 5 | 82000 |

Example 8

Inhibition of IL-1β Secretion from Mixed Population of Peripheral Blood Mononuclear Cells (PBMC)

Processing of pre-IL-1β by caspase-1 can be measured in cell culture using a variety of cell sources. Human PBMC obtained from healthy donors provides a mixed population of lymphocyte and mononuclear cells that produce a spectrum of interleukins and cytokines in response to many classes of physiological stimulators.

Experimental Procedure

The test compound is dissolved in Dimethyl Sulphoxide (DMSO, Sigma #D-2650) to give a 100 mM stock solution. This is diluted in complete medium consisting of RPMI containing 10% heat inactivated FCS (Gibco BRL #10099-141), 2 mM L-Glutamine (Sigma, #G-7513), 100 U penicillin and 100 μg/ml streptomycin (Sigma #P-7539). The final concentration range of test compound is from 100 μM down to 6 nM over eight dilution steps. The highest concentration of test compound is equivalent to 0.1% DMSO in the assay.

Human PBMC are isolated from Buffy Coats obtained from the blood bank using centrifugation on Ficoll-Paque leukocyte separation medium (Amersham, #17-1440-02) and the cellular assay is performed in a sterile 96 well flat-bottomed plate (Nunc). Each well contains 100 μl of the cell suspension, 1×10$^5$ cells, 50 μl of compound dilutions and 50 μl of LPS (Sigma #L-3012) at 50 ng/ml final concentration. Controls consist of cells +/– LPS stimulation and a serial dilution of DMSO diluted in the same way as compound. The plates are incubated for 16-18 h at 37° C. in 5% CO$_2$ & 95% humidity atmosphere.

After 16-18 h the supernatants are harvested after centrifuging the plates at 100×g at 18° C. for 15 min and assayed for their IL-1β content. Measurement of mature IL-1β in the supernatant is performed using the Quantikine kits (R&D Systems) according to manufacturer's instructions. Mature IL-1β levels of about 600-1500 pg/ml are observed for PBMCs in positive control wells.

The inhibitory potency of the compounds can be represented by an IC$_{50}$ value, which is the concentration of inhibitor at which 50% of the mature IL-1β is detected in the supernatant as compared to the positive controls. Table 7 shows inhibition of IL-1β secretion from peripheral blood mononuclear cells for selected compounds of this invention as determined by the above methods.

TABLE 7

| Inhibition of IL-1β secretion from PBMC | |
| --- | --- |
| Example Number | IC$_{50}$ (nM) |
| 4 | 569 |

Example 9

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 eg the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell based assay to screen compounds for inhibition of the caspase-8-mediated apoptotic pathway.

Experimental Procedure

Jurkat E6.1 cells are cultured in complete medium consisting of RPMI-1640 (Sigma No)+10% foetal calf serum (Gibco BRL No. 10099-141)+2 mM L-glutamine (Sigma No. G-7513). The cells are harvested in log phase of growth. 100 ml Cells at 5-8×10$^5$ cells/ml are transferred to sterile 50 ml Falcon centrifuge tubes and centrifuged for 5 minutes at 100×g at room temperature. The supernatant is removed and the combined cell pellets resuspended in 25 ml of complete medium. The cells are counted and the density adjusted to 2×10$^6$ cells/ml with complete medium.

The test compound is dissolved in dimethyl sulphoxide (DMSO) (Sigma No. D-2650) to give a 100 mM stock solution. This is diluted to 400 μM in complete medium, then serially diluted in a 96-well plate prior to addition to the cell assay plate.

100 μl of the cell suspension (2×10⁶ cells) is added to each well of a sterile 96-well round-bottomed cluster plate (Costar No. 3790). 50 μl of compound solution at the appropriate dilution and 50 μl of anti-Fas antibody, clone CH-11 (Kamiya No. MC-060) at a final concentration of 10 ng/ml, are added to the wells. Control wells are set up minus antibody and minus compound but with a serial dilution of DMSO as vehicle control. The plates are incubated for 16-18 hrs at 37° C. in 5% $CO_2$ and 95% humidity.

Apoptosis of the cells is measured by the quantitation of DNA fragmentation using a 'Cell Death Detection Assay' from Boehringer-Mannheim, No. 1544 675. After incubation for 16-18 hrs the assay plates are centrifuged at 100×g at room temperature for 5 minutes. 150 μl of the supernatant are removed and replaced by 150 μl of fresh complete medium. The cells are then harvested and 200 μl of the lysis buffer supplied in the assay kit are added to each well. The cells are triturated to ensure complete lysis and incubated for 30 minutes at 4° C. The plates are then centrifuged at 1900×g for 10 minutes and the supernatants diluted 1:20 in the incubation buffer provided. 100 μl of this solution is then assayed exactly according to the manufacturer's instructions supplied with the kit. $OD_{405}$ nm is measured 20 minutes after addition of the final substrate in a SPECTRAmax Plus plate reader (Molecular Devices). $OD_{405}$ nm is plotted versus compound concentration and the $IC_{50}$ values for the compounds are calculated using the curve-fitting program SOFTmax Pro (Molecular Devices) using the four parameter fit option.

Table 8 shows the results of the activity of selected compounds of this invention in the FAS induced apoptosis assay.

TABLE 8

| Activity in FAS Induced Apoptosis Assay | |
|---|---|
| Example Number | $IC_{50}$ (nM) |
| 6 | 168 |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:
1. A compound of formula I:

or a pharmaceutically acceptable salt thereof, wherein:
$R^1$ is hydrogen, $CHN_2$, R, or —$CH_2Y$;
R is an aliphatic group, an aryl group, an aralkyl group, a heterocyclic group, or a heterocyclylalkyl group;
Y is group halogen, arylsulfonyloxy, alkylsulfonyloxy, trifluoromethanesulfonyloxy, OR, SR, —OC=O(R), or —$OPO(R^3)(R^4)$;

$R^2$ is $CO_2H$, $CH_2CO_2H$; an ester of $CO_2H$ or $CH_2CO_2H$; or an amide of $CO_2H$ or $CH_2CO_2H$ selected from the group consisting of $C_{1-12}$ aliphatic esters, aryl esters, aralkyl esters, heterocyclyl esters, heterocyclylalkyl esters; $C_{1-12}$ aliphatic amides, aryl amides, aralkyl amides, keterocyclyl amides, and heterocyclylalkyl amides; or $R^2$ is an isostere of $CO_2H$ or $CH_2CO_2H$ selected from the group consisting of $CONHSO_2$(alkyl) and $CH_2CONHSO_2$(alkyl);
$X_2$—$X_1$ is $C(R^3)_2$—$C(R^3)$, $C(R^3)$=C, C(=O)—$C(R^3)$;
each $R^3$ is independently selected from hydrogen or $C_{1-6}$ aliphatic,
Ring C is a fused aryl ring;
n is 0, 1 or 2; and
each methylene carbon in Ring A is optionally and independently substituted by =O, or by one or more halogen, $C_{1-4}$ alkyl, or $C_{1-4}$ alkoxy.

2. The compound of claim 1 having one or more of the following features:
(a) $R^1$ is —$CH_2Y$ wherein Y is a halogen, OR, SR, or —OC=O(R), wherein R is an aryl group or heterocyclic group;
(b) $R^2$ is $CO_2H$, $CH_2CO_2H$; an ester of $CO_2H$ or $CH_2CO_2H$; or an amide of $CO_2H$ or $CH_2CO_2H$ selected from the group consisting of $C_{1-12}$ aliphatic esters, aryl esters, aralkyl esters, heterocyclyl esters, heterocyclylalkyl esters; $C_{1-12}$ aliphatic amides, aryl amides, aralkyl amides, keterocyclyl amides, and heterocyclylalkyl amides; or $R^2$ is an isostere of $CO_2H$ or $CH_2CO_2H$ selected from the group consisting of $CONHSO_2$(alkyl) and $CH_2CONHSO_2$(alkyl);
(c) $X_2$—$X_1$ is $C(R^3)$=C;
(d) Ring C is a fused five or six-membered aromatic ring having zero to two heteroatoms; and
(e) n is 0 or 1.

3. The compound of claim 2 wherein:
(f) $R^1$ is —$CH_2Y$ wherein Y is a halogen, OR, SR, or —OC=O(R), wherein R is an aryl group or heterocyclic group;
(g) $R^2$ is $CO_2H$, $CH_2CO_2H$; an ester of $CO_2H$ or $CH_2CO_2H$; or an amide of $CO_2H$ or $CH_2CO_2H$ selected from the group consisting of $C_{1-12}$ aliphatic esters, aryl esters, aralkyl esters, heterocyclyl esters, heterocyclylalkyl esters; $C_{1-12}$ aliphatic amides, aryl amides, aralkyl amides, keterocyclyl amides, and heterocyclylalkyl amides; or $R^2$ is an isostere of $CO_2H$ or $CH_2CO_2H$ selected from the group consisting of $CONHSO_2$(alkyl) and $CH_2CONHSO_2$(alkyl);
(h) $X_2$—$X_1$ is $C(R^3)$=C;
(i) Ring C is a fused five or six-membered aromatic ring having zero to two heteroatoms; and
(j) n is 0 or 1.

4. The compound of claim 3 wherein $R^1$ is —$CH_2Y$ wherein Y is F; $R^2$ is $CO_2H$, $CH_2CO_2H$; an ester of $CO_2H$ or $CH_2CO_2H$; or an amide of $CO_2H$ or $CH_2CO_2H$ selected from the group consisting of $C_{1-12}$ aliphatic esters, aryl esters, aralkyl esters, heterocyclyl esters, heterocyclylalkyl esters; $C_{1-12}$ aliphatic amides, aryl amides, aralkyl amides, keterocyclyl amides, and heterocyclylalkyl amides; or $R^2$ is an isostere of $CO_2H$ or $CH_2CO_2H$ selected from the group consisting of $CONHSO_2$(alkyl) and $CH_2CONHSO_2$(alkyl); $X_2$—$X_1$ is CH=C; Ring C is benzene ring; and n is 0 or 1.

5. The compound of claim 1, said compound selected from the following compounds

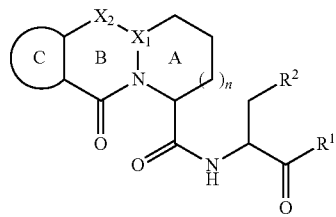

| Example | R¹ | R² | Ring C | n | X₁ | X₂ |
|---------|-----|-----|--------|---|-----|-----|
| 3 | CH₂F | CO₂H | Benzo | 0 | C | C—H |
| 4 | CH₂F | CO₂H | Benzo | 1 | C | C—H | wherein the bond order between $X_1$ and $X_2$ is a double bond.

6. A pharmaceutical composition comprising a compound as claimed in claim 1 and a pharmaceutically acceptable carrier.

7. A method for treating a disease or condition selected from osteoarthritis, rheumatoid arthritis, cell preservation, or organ preservation, comprising administering to a mammal in need of such a treatment a therapeutically effective amount of a compound as claimed in claim 1.

8. A method of preserving cells, said method comprising the step of bathing the cells in an effective amount of a solution of a compound as claimed in claim 1.

9. A method of preserving an organ for organ transplant or for preserving a blood product, comprising the step of bathing the organ or blood product in an effective amount of a solution of a compound as claimed in claim 1.

* * * * *